US009302041B2

(12) United States Patent  
Stacey

(10) Patent No.: US 9,302,041 B2  
(45) Date of Patent: Apr. 5, 2016

(54) BLOOD-DONATION SYSTEM

(71) Applicant: Haemonetics Corporation, Braintree, MA (US)

(72) Inventor: Gary R. Stacey, Marshfield, MA (US)

(73) Assignee: Haemonetics Corporation, Braintree, MA (US)

(*) Notice: Subject to any disclaimer, the term of this patent is extended or adjusted under 35 U.S.C. 154(b) by 286 days.

(21) Appl. No.: 13/833,873

(22) Filed: Mar. 15, 2013

(65) Prior Publication Data

US 2014/0266743 A1    Sep. 18, 2014

(51) Int. Cl.

| | |
|---|---|
| *A61M 1/38* | (2006.01) |
| *A61B 19/00* | (2006.01) |
| *A61G 99/00* | (2006.01) |
| *G05B 19/04* | (2006.01) |
| *A61M 1/02* | (2006.01) |
| *A61G 13/10* | (2006.01) |

(52) U.S. Cl.
CPC .................. *A61M 1/38* (2013.01); *A61B 19/44* (2013.01); *A61G 99/00* (2013.01); *A61M 1/02* (2013.01); *G05B 19/04* (2013.01); *A61B 2019/448* (2013.01); *A61G 13/102* (2013.01)

(58) Field of Classification Search
CPC ... A61M 1/38; A61M 1/0209; A61M 1/3693; A61M 1/30; B01D 61/22; G05B 19/04; G05B 19/0421; A61B 5/14; A61B 5/0022; G06F 19/3418
USPC ................ 340/603, 4.3, 4.31, 539.12, 573.1; 210/739, 782; 604/6.15, 6.01, 6, 5.01, 604/4, 4.01, 131, 134
See application file for complete search history.

(56) References Cited

U.S. PATENT DOCUMENTS 4,842,576 A * 6/1989 Lysaght et al. ............... 604/6.01  
4,911,703 A   3/1990 Lysaght et al. .................... 604/6

(Continued)

FOREIGN PATENT DOCUMENTS

| CN | 2870807 | 2/2007 | ............. A61G 15/00 |
| EP | 2 438 897 | 4/2012 | ............... A61G 7/05 |
| KR | 10-1378141 | 3/2014 | ............... A47C 7/46 |

OTHER PUBLICATIONS

Blaine R. Copenheaver, Authorized officer Commissioner for Patents, United States Patent and Trademark Office, International Search Report—Application No. PCT/US2014/028424, mailed Aug. 11, 2014, 12 pages, including Written Opinion of the International Searching Authority.

(Continued)

*Primary Examiner* — Hung T Nguyen  
(74) *Attorney, Agent, or Firm* — Sunstein Kann Murphy & Timbers LLP

(57) ABSTRACT

A blood-donation system and methods of usage are disclosed. The system includes a blood-donating chair configured to interoperate with various blood-processing apparatuses. The system further combines into a self-contained system all devices, communications pathways and power supplies for various powered devices employed during a blood-collecting session. The system may further interoperate with other blood-donation systems allowing for continuous monitoring of multiple blood-collecting sessions at a single user interface. According to another embodiment, in addition to interoperability, the system is further configured for upgradability, in which, various donor-station devices may be mounted and remounted.

27 Claims, 8 Drawing Sheets

(56) References Cited

U.S. PATENT DOCUMENTS

| | | | |
|---|---|---|---|
| 4,964,976 A * | 10/1990 | Lysaght et al. | 210/650 |
| 6,102,883 A * | 8/2000 | Kingsley et al. | 604/6.02 |
| 7,708,710 B2 * | 5/2010 | Min et al. | 604/6.01 |
| 2003/0040835 A1 | 2/2003 | Ng et al. | 700/214 |
| 2003/0128125 A1 | 7/2003 | Burbank et al. | 340/605 |
| 2003/0154108 A1 * | 8/2003 | Fletcher-Haynes | G06Q 50/24 705/3 |
| 2008/0235872 A1 | 10/2008 | Newkirk et al. | 5/600 |
| 2010/0112513 A1 | 5/2010 | Fröjdman et al. | 433/33 |
| 2010/0249545 A1 | 9/2010 | Copeland et al. | 600/306 |
| 2012/0036638 A1 | 2/2012 | Penninger et al. | 5/610 |
| 2012/0089419 A1 | 4/2012 | Huster et al. | 705/3 |
| 2012/0215360 A1 | 8/2012 | Zerhusen et al. | 700/275 |
| 2014/0266743 A1 | 9/2014 | Stacey | 340/603 |

OTHER PUBLICATIONS

YouTube, Arelmedical Model 2077 (Motorized) Dialysis & Blood Donor Chair, YouTube [Online], Jun. 11, 2012 https://www.youtube.com/watch?v=z6roNHWK8To.

* cited by examiner

BLOOD-DONATION SYSTEM

TECHNICAL FIELD

The present invention relates to blood-collection, and more particularly to a blood-donation system and usage thereof for collecting blood or blood components.

BACKGROUND

Current methods for collecting blood—whether they are for apheresis or whole-blood collection—typically use a variety of stand-alone products, such as RFID or bar-code scanners, pressure cuffs, RF tube sealers and shakers. Apheresis systems also use a separation device, typically one that uses centrifugation. Users of these current methods typically mix and match products from multiple vendors.

In addition, the multitude of devices used in collecting blood or blood components can prevent practical access to AC power on mobile blood drives, often forcing an over-reliance on batteries. However, this forces users of the current blood-collection methods to need to regularly recharge multiple types of batteries with non-compatible chargers. Another, related common problem with having to use so many different battery-powered devices in collecting blood is that battery packs exhaust themselves at different times often without warning.

Handheld data devices have not worked well in this context, because they are too heavy and awkward to hold, they are expensive, they have limited battery life, they have a small display and keyboard, and they are prone to dropping and loss. Also, having to hold a data device hinders an operator from having both hands free to attend to donor.

SUMMARY OF THE EMBODIMENTS

In one embodiment, a blood-donation system of the present invention includes a blood-donating chair, and a controller affixed to or removable from the blood-donating chair. The controller is configured to operatively link at a first time with a first blood-processing apparatus and at a second time with a second blood-processing apparatus, wherein the blood-processing apparatuses receive and treat blood from donors. In a particular embodiment, each of the first and second blood-processing apparatuses may be a whole-blood collection system, a blood shaker system, or a blood-component separation system. In a further particular embodiment, each of the first and second blood-processing apparatuses is a blood-component separation system, which more particularly may be an apheresis system, such as a platelet apheresis system, a red-blood cell apheresis system, a double red-blood cell apheresis system, a red-blood cell and plasma apheresis system, or a plasma apheresis system.

In a preferred embodiment, the blood-donating chair includes a user interface and the first and second blood-component separation systems do not include user interfaces. In this embodiment, the user interface of the blood-donating chair sends commands to and receives data from the first and second blood-component separation systems. In particular embodiments, this user-interface includes a touch screen or includes a display and a keyboard.

In another preferred embodiment, which may or may not be combined with the user-interface embodiment described above, the blood-donating chair includes a power supply that supplies power to the first and second blood-component separation systems, which systems preferably lack their own power supplies.

In another preferred embodiment, which may or may not be combined with embodiments described above, the blood-donating chair has a plurality of mounting members configured to mount and remount a plurality of donor-station devices—such as a compressor cuff assembly, and/or a shaker assembly, and/or a tube clamp assembly, and/or a tube sealer assembly, and/or a blood-bag identification scanner or reader.

In a further preferred embodiment, the blood-donating chair includes a power supply that supplies power to at least several of the donor-station devices. This power supply may be the same as the power supply for the first and second blood-component separation systems, referred to above. In addition, a user interface of the blood-donating chair may be used to send commands to and/or receive data from the several of the donor-station devices, which preferably lack their own user interfaces—and preferably lack their own power supplies.

In another preferred embodiment, which may or may not be combined with embodiments described above, the controller has a communication port configured to operatively link with a second controller of a second blood-donation system, so that the controller may cause status information from the second controller to be shown on a display on the first blood-donating chair.

In another embodiment, which may or may not be combined with embodiments described above, a blood-donation system of the present invention includes, in addition to a blood-donating chair, an energy storage unit configured to provide power for a plurality of donor-station devices, and an external power cable, connected to the energy-storage unit, for connecting to an external power supply. A controller affixed to or removable from the blood-donating chair may control the energy-storage unit. The energy storage unit preferably includes a recharger for recharging a battery with energy from the external power supply. The energy storage unit also preferably includes a switch for automatically switching between providing power to the plurality of donor-station devices from the external power cable or from the battery. The energy storage unit also preferably includes a second battery.

A process according to one embodiment includes the steps of providing a blood-donating chair having a controller configured to operatively link at a first time with a first blood-processing apparatus and at a second time with a second blood-processing apparatus, unlinking the controller and the first blood-processing apparatus, and linking the controller to the second blood-processing apparatus. In a preferred embodiment, the blood-processing apparatuses are apheresis systems.

A process according to another embodiment is directed to upgrading a blood-donation system and includes the steps of providing a blood-donating chair configured to mount and remount a plurality of donor-station devices, the blood-donating chair having at least one donor-station device mounted thereon; dismounting the donor-station device; and mounting the upgraded donor-station device.

A process according to another embodiment is also directed to upgrading a blood-donation system and includes the steps of providing a controller for a blood-donating chair configured to operatively link with a first blood-donating apparatus, wherein the controller is configured to i) receive status information from blood-donating apparatuses and ii) transmit commands to blood-donating apparatuses before, during or after a blood-drawing session, the controller having a display having a first format associated with status information and a second format associated with a control sequence, the first and second formats being associated with the first blood-donating apparatus; replacing the first blood-donating apparatus with a second blood-donating apparatus; linking the second blood-donating apparatus to the controller; and configuring the controller in a manner that the first and second formats associated with the second blood-donating apparatus remain substantially the same as the first and second formats associated with the first blood-donating apparatus. In a particular embodiment, the first and second blood-donating apparatuses include a blood-processing apparatus selected from a group consisting of a whole-blood collection system, a blood shaker system, and a blood-component separation system, and/or they may include a donor-station device selected from a group consisting of a compressor cuff assembly; a shaker assembly; a tube clamp assembly; a tube sealer assembly; a blood-bag identification scanner; and a blood-bag identification reader. In a preferred embodiment, the blood-processing apparatuses are apheresis systems.

A process according to one embodiment includes the steps of providing a controller of a first blood-donation system having a communication port to operatively link to a second controller of a second blood-donation system, the controller being configured, via the communication port, to receive status information of a blood-drawing session of the second blood-donation system, the controller located in or on a blood-donating chair; initiating a first blood-drawing session at the first blood-donation system; initiating a second blood-drawing session at the second blood-donation system, the second blood-drawing session being at least partially concurrent with the first blood-drawing session; and displaying status information of the first and second blood-drawing sessions at a display mounted on the blood-donating chair.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions

As used in this description and the accompanying claims, the following terms shall have the meanings indicated, unless the context otherwise requires:

A "blood-donating chair" is any piece of furniture for receiving and holding a blood donor during the process of blood donation. For example, a blood-donating chair may include a bed, such as an adjustable hospital-type bed or a stretcher; a chair, such as a stroller or a motorized chair; or a table upon which a donor may lie, and may include beds, tables, or chairs that fold and/or are portable.

A "format" includes a display arrangement for status information, commands, sequences of command, and/or data transmission and reception sequences.

When a device or component is described as "in" the blood-donating chair, that component may be located in or on the blood-donating chair—and similarly, when a device or component is described as "on" the blood-donating chair, that component may be located in or on the blood-donating chair.

In a preferred embodiment of the present invention, a central unit—preferably a blood-donation chair—is used to integrate all the devices used in collecting blood or blood components in unified communication and power pathways.

In current methods, many of the devices used in collecting blood or blood components generally have their own displays, controls, batteries or other power systems, and/or communication links. All this duplication increases the complexity of operation, the weight of the system, and its respective cost. Additionally, the duplication provides opportunity for errors in providing choices, requires training, different standard operating procedures (SOPs), as well as the time and costs for engineering and regulatory compliance. And this duplication decreases usability, reliability and efficiency.

Figure 1:
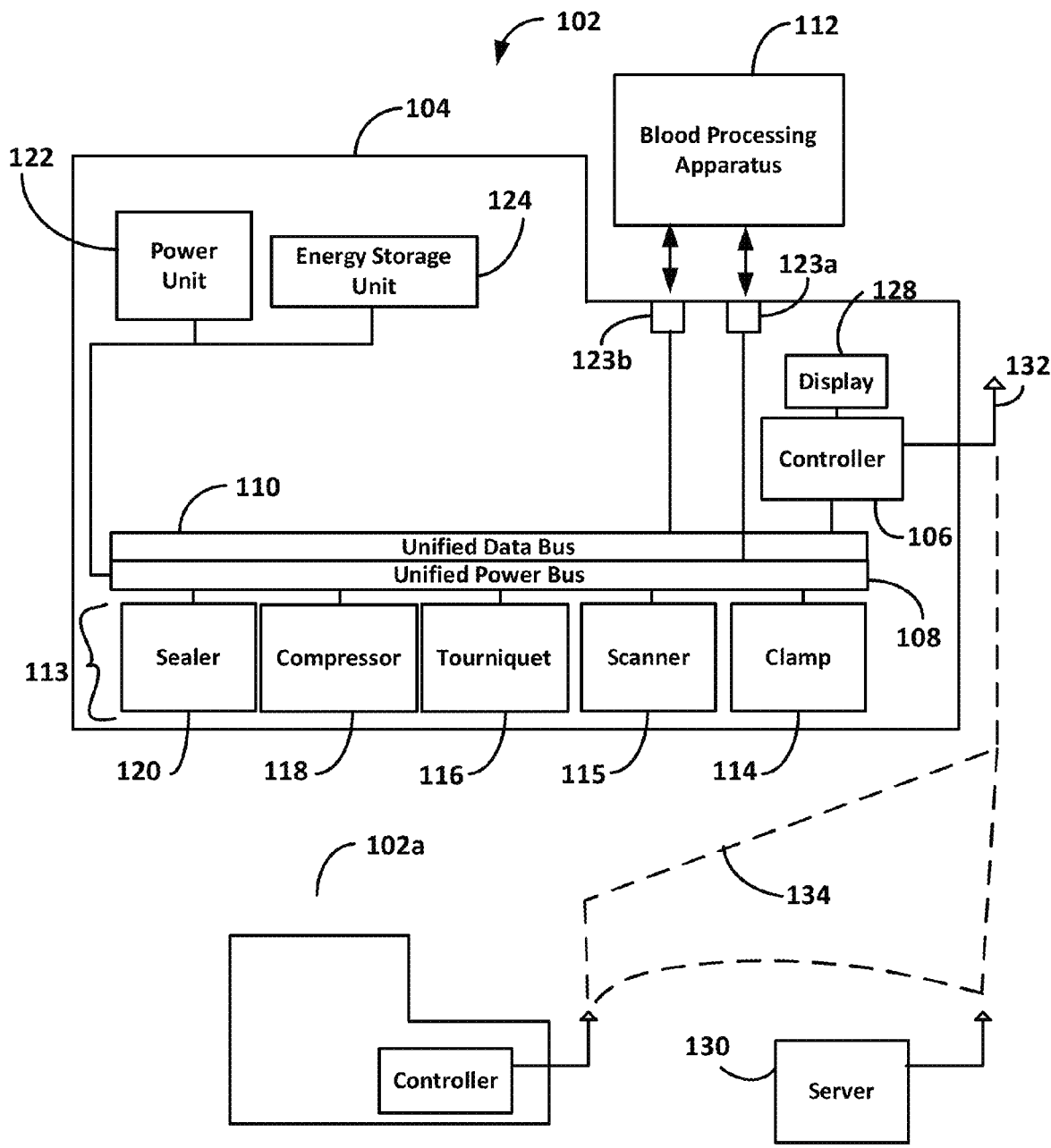
FIG. 1 is a diagram that schematically illustrates a blood-donation system according to an illustrative embodiment.

FIG. 1 is a diagram that schematically illustrates a blood-donation system 102 according to an illustrative embodiment. The system 102 includes a blood-donating chair 104 and a controller 106. The blood-donating chair 104 provides, in effect, a power bus 108 and a data-bus (or data/control bus) 110 for a blood-processing apparatus 112 and donor-station devices 113. These buses may, of course, be combined into a single bundle of wires. The controller may control the passage of data over the data bus and may also control the supply of power to the blood-processing apparatus 112 and donor-station devices 113. The controller 106 may be adapted to be affixed to the blood-donating chair 104, as well as to be dismounted therefrom. The controller 106 may be configured to connect through the unified data-bus 110 with a blood-processing apparatus 112 and donor-station devices 113, so as to control them. The blood-processing apparatus 112 generally refers to an external device that processes or treats the blood subsequent to it being drawn or collected from the donor lying on the blood-donating chair 104.

The blood-processing apparatus may include, for example, blood-component separation systems, such as apheresis systems (e.g., a platelet apheresis system; a red-blood cell apheresis system; a double red-blood cell apheresis system; a red-blood cell and plasma apheresis system; and a plasma apheresis system), and whole-blood collection systems, as well as blood shaker systems. This blood-processing apparatus may be external to the blood-donating chair, especially if it is relatively bulky or if it might create vibrations that are uncomfortable to the donor, as may be the case with a centrifuge-based apheresis system. Donor-station devices 113 are generally those devices that would preferably be maintained at or near a donor station for handling the blood-bag and/or for otherwise assisting in the blood-draw. The donor-station devices 113 may include an electric or pneumatically-powered tube clamp 114 for a blood-processing system (e.g., a blood shaker system); a bar-code/radio-frequency identification device (RFID) scanner 115 for scanning the bar code or RFID of a blood-bag; an electric or pneumatically-powered tourniquet or compressing cuff system 116; an electric compressor 118 to provide high-pressure air for the donor-station devices 113, such as the tube clamp 114 or the automatic tourniquet 116; and an electric high-frequency tube sealer 120 for the blood-bags.

The system 102 further includes a power unit 122 configured to provide power to the unified power-bus 108 for the donor-station devices 113 and the blood-processing apparatus 112 operatively connected thereto. The unified power-bus 108 may terminate at a connector 123a adapted to connect to the blood-processing apparatus 112. The power unit 122 may be coupled to an energy storage unit 124 (i.e., batteries) affixed to the blood-donating chair 104. The energy storage unit 124 may include at least two battery units 126 (not shown) for redundancy.

According to the illustrative embodiment, several unifying features have been employed for the power unit 122. The power unit 122 may operate from single power plug (referred to as AC plug) while providing electrical receptacles in the blood-donating chair 104 for the donor-station devices 113. In an embodiment, the energy storage unit 124 may be coupled to the power-bus 108. The power unit 122 may provide power to the power-bus 108 to charge and recharge the batteries from the single plug. Alternatively, the system 102 may include a transfer switch (not shown) to select between the two batteries in the energy storage unit 124 and allow one battery to be recharged while allowing energy to be drawn from the other battery. Having just one external AC plug per chair greatly simplifies the powering of all the devices at a mobile blood drives, including the donor-station devices 113 and the blood-processing apparatus 112. Also, recharging is much simpler with such an arrangement. The dual, redundant battery system may increase reliability and predictability.

According to another embodiment, the power unit 122 may include an AC-to-DC converter to provide DC power to the unified power-bus 108. As such, donor station devices 113 that operate with DC power may link to the DC portion of the power-bus 108, thereby centralizing the energy conversion at the blood-donating chair 104.

Also, the system 102 may employ a unified data-bus 110 in the blood-donating chair 104. The unified data-bus 110 may terminate at a data connector 123b affixed to the blood-donating chair 104. The multiple data paths (wired and particularly wireless) that are found in current blood-collection methods create additional opportunity for failure and compatibility issues. Providing a single data link through the blood-donating chair 104 reduces these issues. Additionally, through connector 123b, control and status links between the controller 106 and the blood-processing apparatus 112 may be provided via the data-bus 110. As such, the display panel of the blood-processing apparatus 112 and the donor-station device 113 may be replicated or (preferably) incorporated into a unified display 128 of the controller 106.

The display 128 in conjunction with the controller 106 may be used to allow the user of the blood-donation system 102 to interface with a variety of devices used at a donor station. The display 128 is preferably a touch-screen, so as to allow commands to be sent directly from the display 128. Alternatively, a keyboard and a pointing input device (e.g., mouse) may be provided with the display. By providing a single display for all (or most) of the devices at a donor station, the operator needs to consult only a single display for information about each of the relevant devices, and the operator may enter commands at a single location—thereby making the operator more efficient. This simplification further reduces the risk of errors. This display may also be capable of showing the status of other donor stations. Thus, the donor-station devices 113 or blood-processing apparatus 112 may employ the controller 106 and display 128 as their display and I/O. As such, donor station devices 113 or blood-processing apparatus 112 may be design without an independent display, thereby reducing the cost of the respective devices.

In addition to the other advantages, using a single display and a single power source for a variety of devices at a single donor station reduces the overall weight associated with the equipment for a single donor station. Weight reduction is especially valuable for operators that have mobile blood drives.

The single-display arrangement may be employed to ease the transition when a device is switched out or upgraded. Using consistent formats makes it easier for the operator to learn how to use the new device.

The controller 106 may be configured to operate with a various different types of blood-processing apparatuses 112. The operating environment of the controller may 106 be configured to a common standard. As such, although specific processes within a blood-processing apparatus 112 may change, the format for performing a (i) blood-component separation such as platelet apheresis, red-blood cell apheresis, double red-blood cell apheresis, red-blood cell and plasma apheresis, and a plasma apheresis; as well as (ii) whole-blood collection does not have to change from process to process. Similarly, interfaces and control sequences for other blood-processing apparatus 112, such as blood shakers and mixers may be maintained.

The controller 106 may operatively link with a centralized data system 130 (referred to as "server 130") via a wireless communication system 132. The centralized data system 130 may be a part of the hospital network, a blood-bank network, or a local-area network that links to such networks over secure data channel. The centralized data system 130 may include a database and may provide information relating to the donor records and the blood-drawing session. During a blood-drawing session, the controller 106 may show on the display 128, for example, the donor information and donating-session identification, including the blood-bag identification information, donation blood type, etc. The controller 106, via the display 128 or various other input devices, allows an operator to input information about the blood-drawing session to provide to the centralized data system 130. Table 1 provides list of information that may be provided on the display 128.

TABLE 1

| Blood-Drawing Status Information |
| --- |
| Blood-Donating Session Identification Number |
| Donor Identification Information |
| Blood-Type Information |
| Blood-Drawing Session Description |
| Various notes and instructions |
| Status information of the linked Blood-Processing Apparatus |
| Status information of the connected Donor Station Devices |
| Status information of other blood-drawing sessions |
| Status of the current blood-drawing session |

Figure 8:
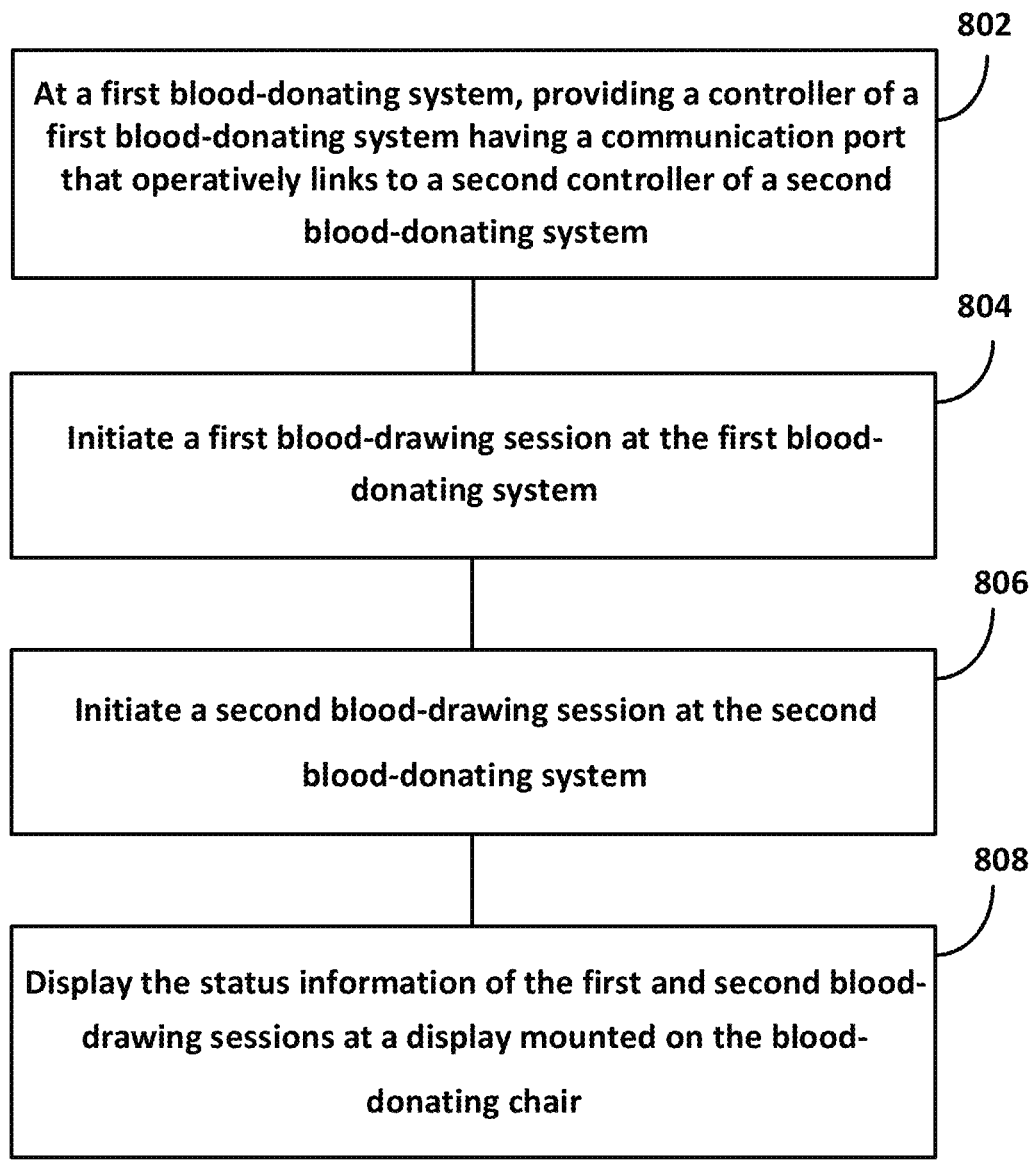
FIG. 8 is a flowchart illustrating a method of operating multiple blood-donation systems according an illustrative embodiment.

As indicated, the controller 106 of a blood-donation system 102 may operatively link other blood-donation systems 102a. FIG. 8 is a flowchart illustrating a method of operating a blood-donation system according to such an illustrative embodiment.

At a first blood-donation system 102, the controller 106 may be linked via the network to the central data system 130 or to other blood-donation systems 102a (step 802). An operator may initiate a blood-donating session at the blood-donation system 102. At the user-interface, during the session or during configuration of the controller 106, the operator may instruct the controller 106 to provide the status information with its network. The controller 106 may periodically broadcast status information during a blood-drawing session. Upon initiating a blood-drawing or blood apheresis session, the controller 106 maintains and monitors a progress status of the various control sequences (step 804). During a portion of the blood-drawing session, the operator may initiate another blood-drawing session with another donor (step 806). The operator may select at the first blood-donation system to display the progress status of the second blood-donating session and the progress status of other blood-donating sessions (step 808).

Figure 4:
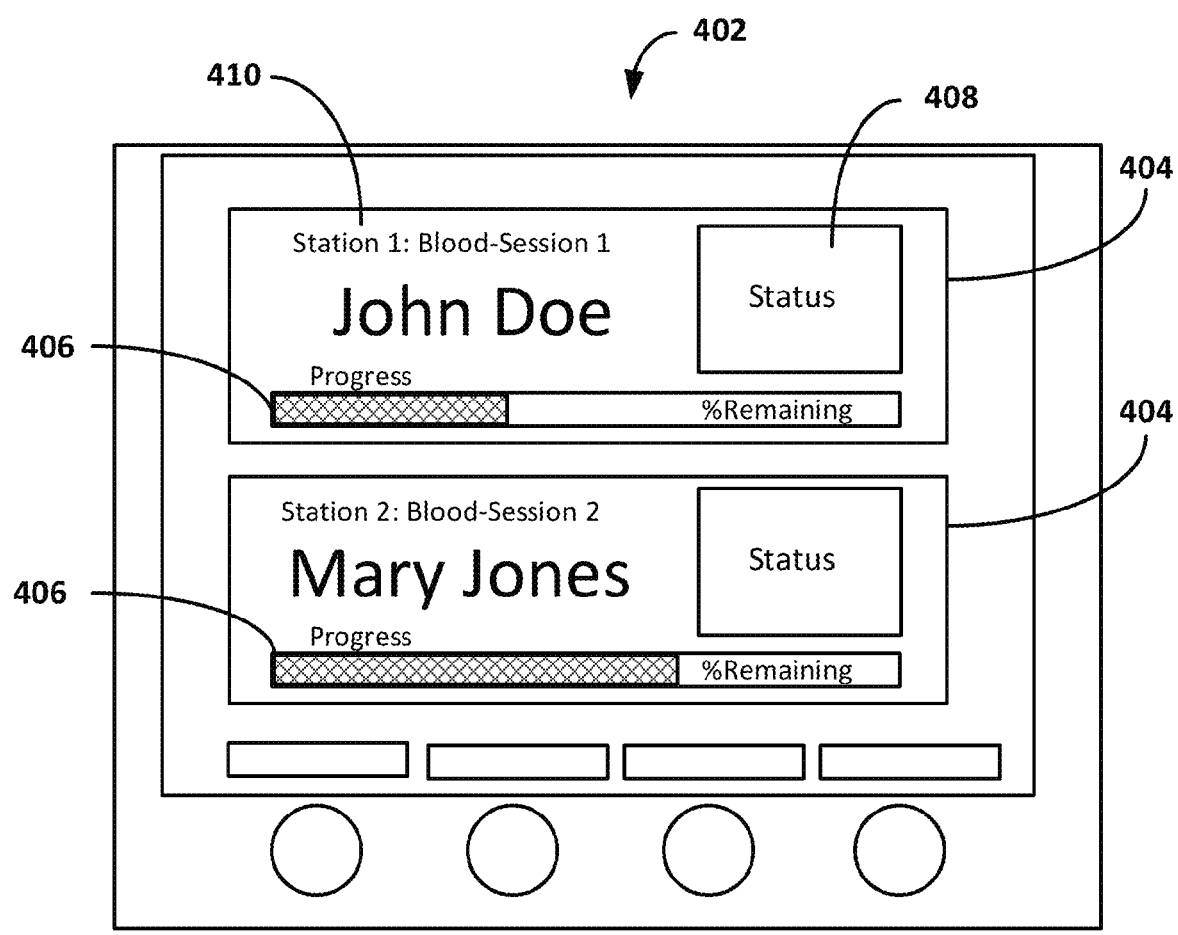
FIG. 4 is a diagram illustrating a user-interface of a blood-drawing session according to an embodiment.

The controller 106 may show, via display 128, the progress and status of the various blood-donating systems 102a in a blood-donating session. FIG. 4 is a diagram illustrating a user-interface 402 of a blood-drawing session. The user-interface 402 may include status information 404 of at least two blood-donation systems 102, 102a. The status information 404 may include a progress indicator 406 for each session, a general status indicator 408, and identifier information 410 for the session.

In accordance with another aspect of the embodiments, the controller 106 and display 128 may replace, augment, or reproduce a display of the blood-processing apparatus 112. The display 128 may include a series of control and status screens that may be toggled via menu buttons therein. The screens may include a summary screen providing the progress of the blood-donating session and session identifier information. The controller 106 may have a different operational screen for each type of blood-processing apparatus 112 or for each type of blood-drawing procedure. As such, the commands of the blood-processing apparatus 112 and the donor-station devices 113 may be provided by the controller 106.

The controller 106 may be configured with an audible alarm corresponding to an error message from a blood-processing apparatus 112 or a donor-station device 113. The controller 106 may be configured to provide an alarm due to loss of power or that back-up power has been engaged.

In a preferable embodiment, the controller 106 may be a low-power device that consumes less than ten watts of power. The controller 106 may employ a static and fan-less heatsink. The display 128 may be at least ten inches in size. The display 128 may be a wide format resistive touch-based LCD panel. The controller 106 may be a standalone processing unit with wire and wireless communication. The unified data-bus 108 may be an Ethernet-based backplane. The data-bus 108 may include a second data-bus that may employ RS-232 or RS-485 communication standards. Of course, other types of data-buses may be used, such as, for example, a peripheral component interconnect (PCI) data-bus. According to another embodiment, the controller 106 may be configured to operatively link (shown as dash-line 134) to other blood-donation systems 102a. As such, multiple blood-drawing sessions may be monitored at each blood-donation system 102. The communication link between the various blood-donation systems 102 may be through the server 130 or it may be directly linked among the various devices.

The blood-donating chair 104 may be adapted to be light-weight. The frame may, for example, be made of bended, machined, welded, or extruded tubes. The unified data-bus 110 and unified power-bus 108 may be affixed within the tubes. In another embodiment, the energy storage unit 124 and portion of the housing for the power unit 122 may be further incorporated into the frame of the blood-donating chair 104.

Figure 2:
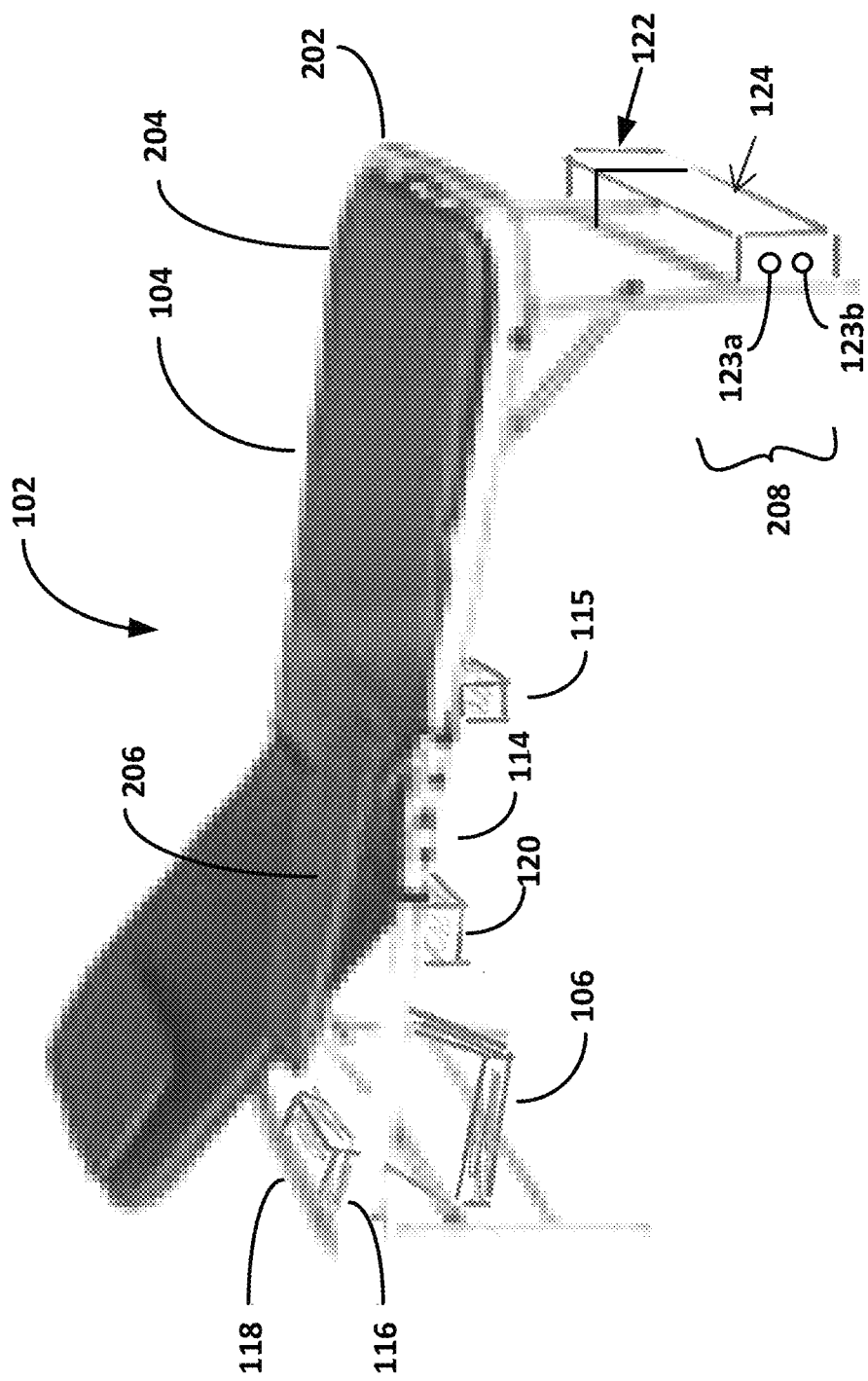
FIG. 2 is a diagram illustrating a blood-donation system according to the illustrative embodiment.

FIG. 2 depicts a blood-donation system 102 according to the illustrative embodiment. As shown, the blood-donation system 102 includes a structural frame 202 that forms or is affixed to a seat member 204. The controller 106 is affixed proximal to an arm rest 206. The controller 106 may be affixed on a hinged assembly allowing it to be rotatably positioned between a right arm-rest (connected to seat member 204) and a left arm-rest (not shown). Alternatively, the blood-donation system 102 may be configured with two docking members configured to allow the controller 106 to dock. As such, an operator may undock the controller from a first docking member and re-dock at a second docking member. As such, each of the docking members is operatively coupled to the unified data-bus 110 and the unified power-bus 108. The automatic tourniquet or compressor cuff 116 may be affixed to the blood-donating chair proximal to the arm-rest 206. The electric air compressor 118 may be mounted proximal to the head of the structural frame 202.

The various donor-station devices 113 may be positioned along the structural frame 202 in a manner to balance the weight distribution. In a preferable embodiment, the compressor may be affixed to the structural member 202 proximal to the feet of the blood-donating chair 104. Additionally, the power unit 122 and energy storage unit 124 may be configured as part of the feet 208 of the structural frame 202 to improve stability of the structure. The blood-bag handling and identification devices, such as the tube clamp 112, the RFID scanner or bar-code scanner 115, and the RF tube sealer 120 may be affixed to the structural frame 202 proximal to the arm-rest 206. The devices may be arranged spatially to correspond to the blood-drawing sequence of the blood-drawing session. The connectors 123a and 123b may be provided at the head end and at the foot end of the blood-donating chair. As such, the blood-processing apparatus 112 may be placed at any of the four corners of the blood-donation system 102 via a cable-power cord.

Figure 3A:
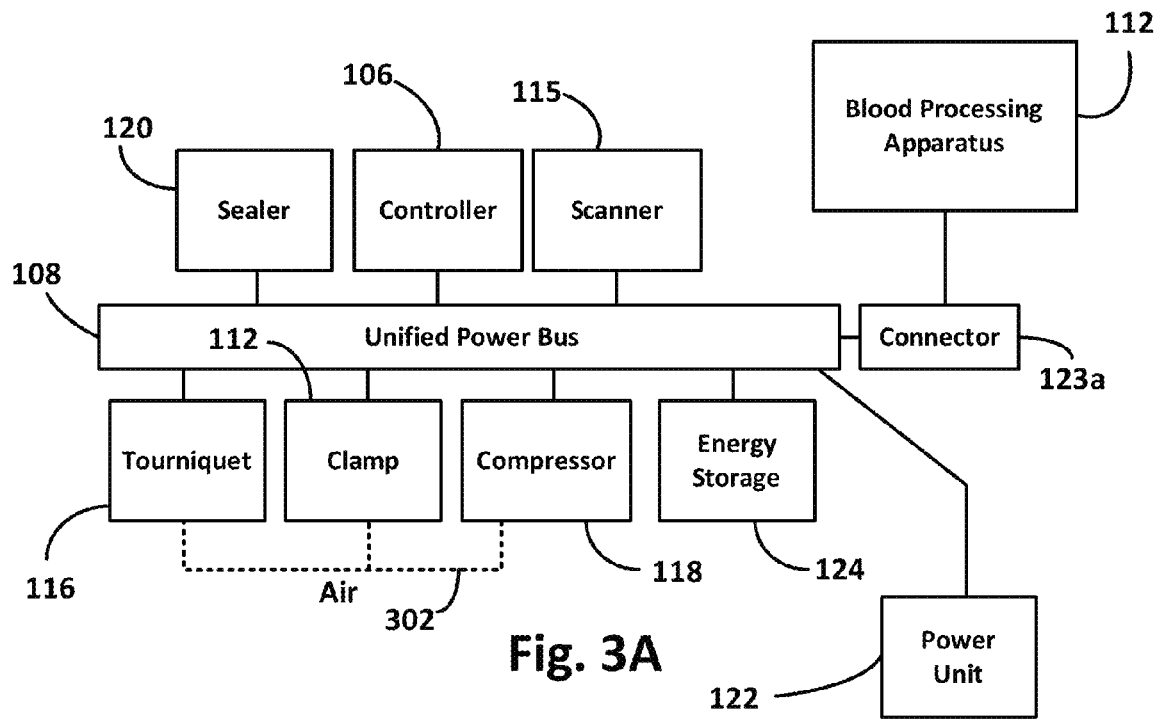
FIG. 3A is a diagram that schematically illustrates the unified power-bus of a blood-donation system according to an illustrative embodiment.

FIG. 3A is a diagram that schematically illustrates a unified power-bus 108 of a blood-donation system 102 according to an illustrative embodiment. An AC bus may also be included and provided with a set of standard AC plug receptacles. The unified power-bus 108 preferably includes a DC bus. The DC bus may provide a 5 VDC, 12 VDC, 24 VDC, and/or 48 VDC output. The DC bus may be combined in a single connector with the data-bus 108. The automatic tourniquet 116 and clamp 114 may be configured to be powered by compressed air from the air-compressor 118 (shown as dash-line 302) or they may be electric and directly couple to the power-bus 108. The unified power-bus 108 may include power ports configured to couple with the donor-station devices 113. As such, the donor-station devices may be powered by the energy-storage unit 124 through the unified power-bus 108.

Figure 3B:
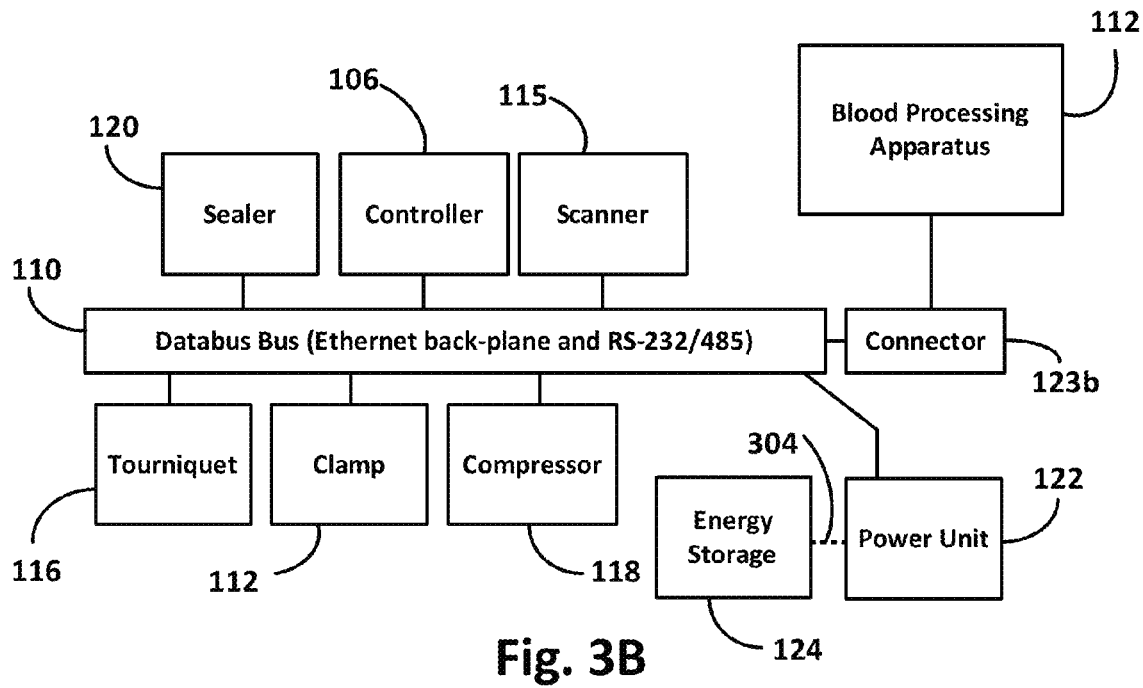
FIG. 3B is a diagram that schematically illustrates a unified data-bus of a blood-donation system according to an illustrative embodiment.

FIG. 3B is a diagram that schematically illustrates a unified data-bus 110 of a blood-donation system 102 according to an illustrative embodiment. The controller 106 may control the various donor-station devices 113 and the blood-processing apparatuses 112 via commands send through the data-bus 110. The controller 106 may further control the power unit 122 through the data-bus 110 as well as receive status information therefrom. The controller 106 may receive energy information corresponding to the energy storage unit 124 via measurement elements (shown as dash-line 304) of the power unit 122.

In a preferable embodiment, the data-bus 110 terminates at connectors configured to receive a data-plug from the donor-station devices 113. In another embodiment, the data-bus includes a back-plane adapted to mate with data-connectors of donor-station devices 113.

Figure 5:
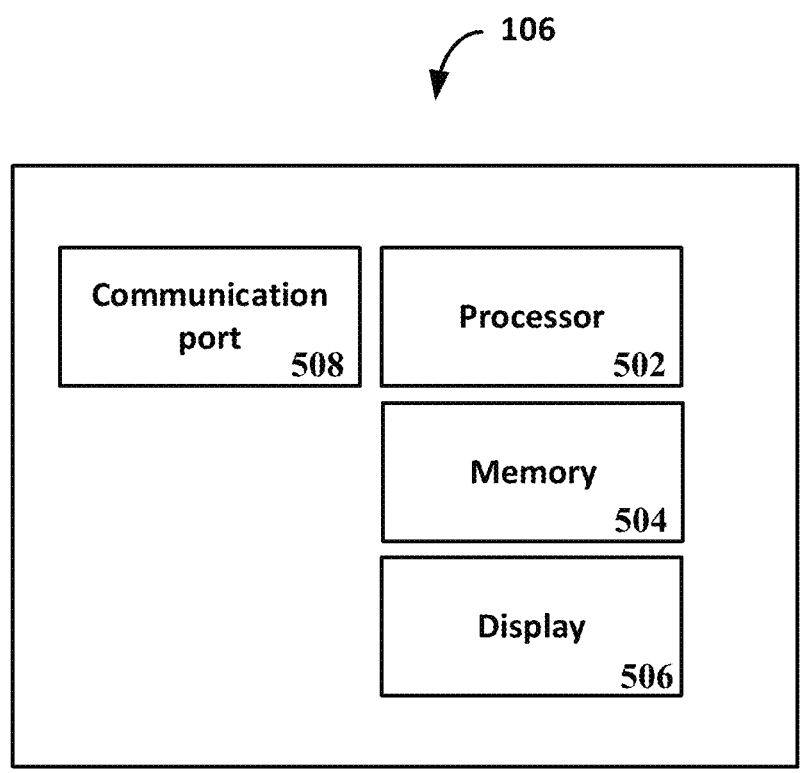
FIG. 5 is a diagram of a controller according to an embodiment.

FIG. 5 is a diagram of a controller 106 according to an illustrative embodiment. The controller 106 may include a processor 502, a memory 504, a display 506, and a communication port 508. The display 506 may correspond to display 128.

Figure 6:
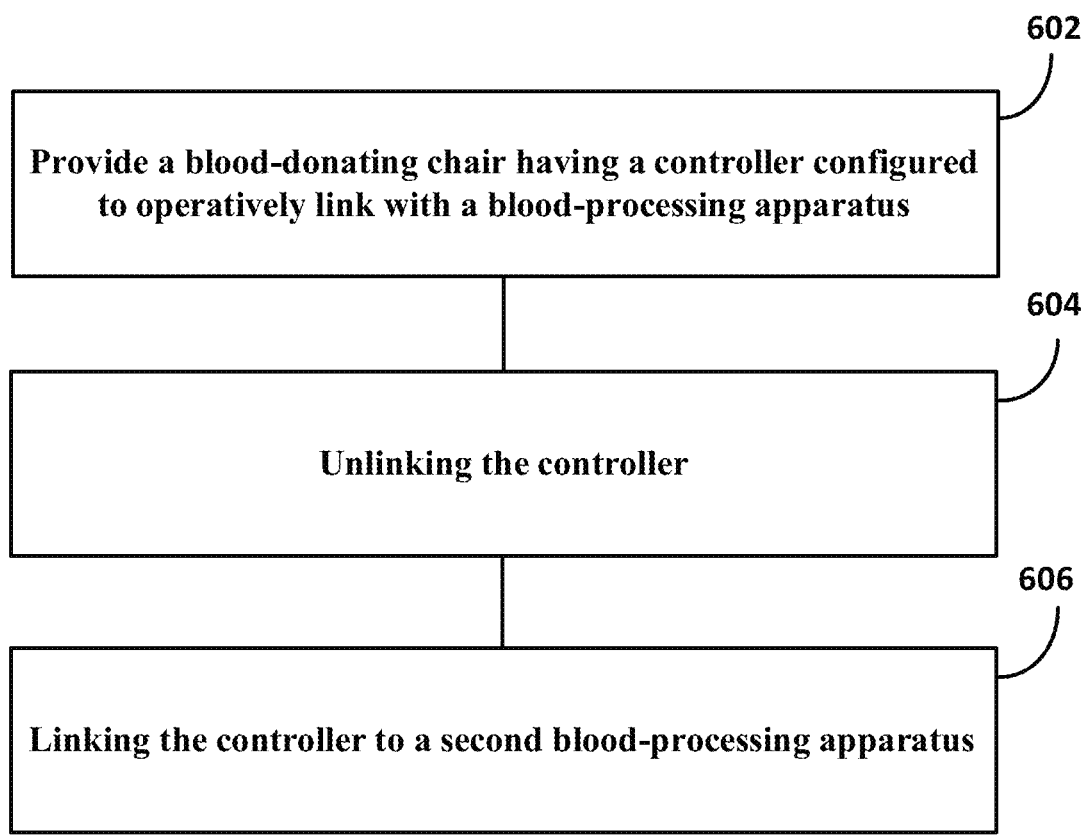
FIG. 6 is a flowchart of a method of operation of the blood-donation system according to an illustrative embodiment.

FIG. 6 is a flowchart of a method of operation of the blood-donation system 102 according to an illustrative embodiment. The controller 106 may be configured to operatively link between various types of blood-processing apparatuses 112. A blood-processing apparatus 112 may be operatively linked to the unified power-bus 108 and to the unified data-bus 110 (step 602). An operator may disconnect the power and data cord between the blood-processing apparatus 112 and the blood-donation system 102 (step 604). A different blood-processing system 112 having a data and power cord configured to couple with the connectors 123a and 123b may be operatively connected. The controller may detect the blood-processing apparatus 102 on the data-bus and may initiate a linking protocol. The linking protocol may include reconfiguring the controls and status elements on the display 128 to link with command and display sets associated with the blood-processing apparatus 112.

Figure 7:
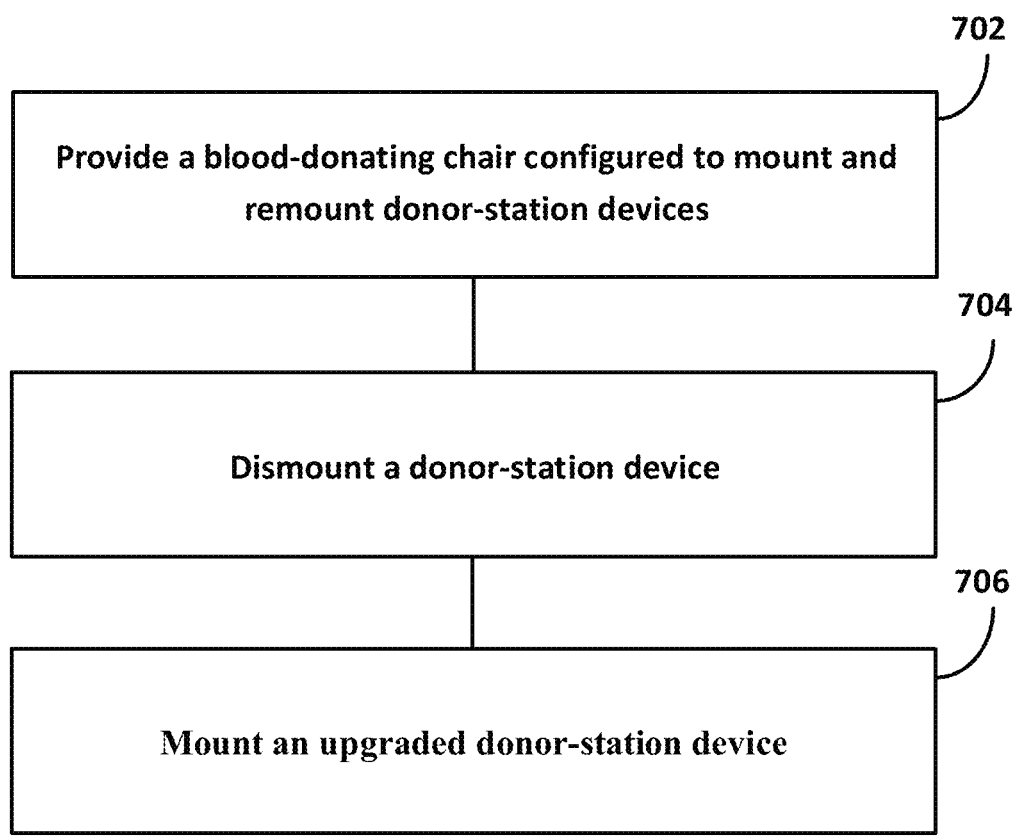
FIG. 7 is a flowchart of a method of upgrading a blood-donation system according to an illustrative embodiment.

FIG. 7 is a flowchart of a method of upgrading a blood-donation system 102 according to an illustrative embodiment. In step 702, a blood-donation system 102 is provided including mountable members configured to receive the various donor-station devices 113. The mounting member may be affixed to the structural frame 202 of the blood-donating chair 104. The mountable members may be in the form of a bracket or housing configured to fixably attach the donor-station device 113 to the structural frame 202. The bracket or housing may be fixably attached to the frame by any of various means, such as screws. The mountable members may include a keying structure (such as a guide) to provide a reference when mounting and unmounting. The donor-station device 113 may have form factors to conform to the physical form of the mounting member. In an alternate embodiment, the mounting member may be a compliant enclosure adapted to receive a donor-station device 113. The enclosure may be a fabric with a fasteners to house and store the donor-station device 113. In step 704, the donor-station device is disconnected from the mounting member, and in step 706, an upgraded donor-station device is connected to the mounting member.

It should be noted that terms such as "controller," "processor" and "server" may be used herein to describe devices that may be used in certain embodiments of the present invention and should not be construed to limit the present invention to any particular device type or system unless the context otherwise requires. Thus, a system may include, without limitation, a client, server, computer, appliance, or other type of device. Such devices typically include one or more network interfaces for communicating over a communication network and a processor (e.g., a microprocessor with memory and other peripherals and/or application-specific hardware) configured accordingly to perform device and/or system functions. Communication networks generally may include public and/or private networks; may include local-area, wide-area, metropolitan-area, storage, and/or other types of networks; and may employ communication technologies including, but in no way limited to, analog technologies, digital technologies, optical technologies, wireless technologies, networking technologies, and internetworking technologies.

The various components of the control program may be implemented individually or in combination. For example, each component may be implemented or a dedicated server or a set of servers configured in a distributed manner.

It should also be noted that devices may use communication protocols and messages (e.g., messages created, transmitted, received, stored, and/or processed by the system), and such messages may be conveyed by a communication network or medium. Unless the context otherwise requires, the present invention should not be construed as being limited to any particular communication message type, communication message format, or communication protocol. Thus, a communication message generally may include, without limitation, a frame, packet, datagram, user datagram, cell, or other type of communication message. Unless the context requires otherwise, references to specific communication protocols are exemplary, and it should be understood that alternative embodiments may, as appropriate, employ variations of such communication protocols (e.g., modifications or extensions of the protocol that may be made from time-to-time) or other protocols either known or developed in the future.

It should also be noted that logic flows may be described herein to demonstrate various aspects of the invention, and should not be construed to limit the present invention to any particular logic flow or logic implementation. The described logic may be partitioned into different logic blocks (e.g., programs, modules, interfaces, functions, or subroutines) without changing the overall results or otherwise departing from the true scope of the invention. Often times, logic elements may be added, modified, omitted, performed in a different order, or implemented using different logic constructs (e.g., logic gates, looping primitives, conditional logic, and other logic constructs) without changing the overall results or otherwise departing from the true scope of the invention.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other programmable logic device (PLD)), discrete components, integrated circuitry (e.g., an Application Specific Integrated Circuit (ASIC)), or any other means including any combination thereof. In a typical embodiment of the present invention, predominantly all of the described logic is implemented as a set of computer program instructions that is converted into a computer executable form, stored as such in a computer readable medium, and executed by a microprocessor under the control of an operating system.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as FORTRAN, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web). Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A blood-donation system comprising:
   a blood-donating chair, the blood-donating chair having a power supply; and
   a controller affixed to or removable from the blood-donating chair, the controller configured to operatively link at a first time with a first blood-processing apparatus and at a second time with a second blood-processing apparatus, the controller configured to control the operation of the first blood-processing apparatus and/or the second blood-processing apparatus, wherein the blood-processing apparatuses receive and treat or process blood from donors, the power supply configured to supply power to the first and second blood-processing apparatuses.

2. The blood-donation system according to claim 1, wherein the first blood-processing apparatus is selected from a group consisting of a whole-blood collection system, a blood shaker system, and a blood-component separation system, and
   wherein the second blood-processing apparatus is selected from a group consisting of a whole-blood collection system, a blood shaker system, and a blood-component separation system.

3. The blood-donation system according to claim 2, wherein the first and second blood-processing apparatuses are blood-component separation systems.

4. The blood-donation system according to claim 3, wherein the blood-component separation systems are selected from a group consisting of a platelet apheresis system; a red-blood cell apheresis system; a double red-blood cell apheresis system; a red-blood cell and plasma apheresis system; and a plasma apheresis system.

5. The blood-donation system according to claim 3, wherein the blood-donating chair includes a user interface and the first and second blood-component separation systems do not include user interfaces, wherein the user interface of the blood-donating chair sends commands to and receives data from the first and second blood-component separation systems.

6. The blood-donation system according to claim 5, wherein the user-interface includes a touch screen.

7. The blood-donation system according to claim 5, wherein the user-interface includes a display and a keyboard.

8. The blood-donation system according to claim 3, wherein the blood-donating chair includes a user interface and the first and second blood-component separation systems do not include user interfaces, wherein the user interface of the blood-donating chair sends commands to and receives data from the first and second blood-component separation systems.

9. The blood-donation system according to claim 1, wherein the blood-donating chair has a plurality of mounting members configured to mount and remount a plurality of donor-station devices.

10. The blood-donation system according to claim 9, wherein the donor-station devices include at least one of:
    a compressor cuff assembly;
    a shaker assembly;
    a tube clamp assembly;
    a tube sealer assembly; or
    a blood-bag identification scanner or reader.

11. The blood-donation system according to claim 9, wherein the power supply is configured to supply power to at least several of the donor-station devices.

12. The blood-donation system according to claim 9, wherein the blood-donating chair includes a user interface and at least several of the donor-station devices do not include user interfaces, wherein the user interface of the blood-donating chair sends commands to and/or receives data from the several of the donor-station devices.

13. The blood-donation system according to claim 12, wherein the power supply is configured to supply power to the several of the donor-station devices.

14. The blood-donation system according to claim 1, wherein the controller has a communication port configured to operatively link with a second controller of a second blood-donation system, the controller configured to display status information from the second controller.

15. A blood-donation system comprising:
    a blood-donating chair;

an energy storage unit configured to provide power for a plurality of donor-station devices, the energy-storage unit having a battery and a plurality of power ports configured to couple with the donor-station devices;

an external power cable, connected to the energy-storage unit, for connecting to an external power supply; and a controller affixed to or removable from the blood-donating chair for controlling the energy-storage unit, wherein the energy storage unit includes a switch for automatically switching between providing power to the plurality of donor-station devices from the external power cable or from the battery.

16. The blood-donation system according to claim 15, wherein the energy storage unit includes a recharger for recharging the battery with energy from the external power supply.

17. The blood-donation system according to claim 16, wherein the energy storage unit includes a second battery.

18. A method of operating a blood-donation system, the method comprising:

providing a blood-donating chair having a controller configured to operatively link at a first time with a first blood-processing apparatus and at a second time with a second blood-processing apparatus, wherein the blood-donating chair includes a power supply that supplies power to the first and second blood-processing apparatuses;

unlinking the controller and the first blood-processing apparatus;

linking the controller to the second blood-processing apparatus; and controlling, using the controller, the operation of the first blood-processing apparatus and/or the second blood-processing apparatus.

19. A method of upgrading a blood-donation system, the method comprising:

providing a blood-donating chair configured to mount and remount a plurality of donor-station devices, the blood-donating chair having at least one donor-station device mounted thereon;

dismounting the donor-station device; and mounting the upgraded donor-station device.

20. A method of upgrading a blood-donation system, the blood-donation system being capable of controlling blood-donating apparatuses, the method comprising:

providing a controller for a blood-donating chair configured to operatively link with a first blood-donating apparatus operatively connected to the blood-donating chair, wherein the controller is configured to i) receive status information from blood-donating apparatuses and ii) transmit commands to blood-donating apparatuses before, during or after a blood-drawing session, the controller having a display having a first format associated with status information and a second format associated with a control sequence, the first and second formats being associated with the first blood-donating apparatus;

replacing the first blood-donating apparatus with a second blood-donating apparatus by disconnecting the first blood-donating apparatus from the blood-donating chair and operatively connecting the second blood-donating apparatus to the blood-donating chair;

linking the second blood-donating apparatus to the controller; and configuring the controller in a manner that the first and second formats associated with the second blood-donating apparatus remain substantially the same as the first and second formats associated with the first blood-donating apparatus.

21. A method according to claim 20, wherein the first and second blood-donating apparatuses include a blood-processing apparatus selected from a group consisting of a whole-blood collection system, a blood shaker system, and a blood-component separation system.

22. A method according to claim 20, wherein the first and second blood-donating apparatuses include a donor-station device selected from a group consisting of a compressor cuff assembly; a shaker assembly; a tube clamp assembly; a tube sealer assembly; a blood-bag identification scanner; and a blood-bag identification reader.

23. A method of operating a blood-donation system comprising:

providing a controller of a first blood-donation system having a communication port to operatively link to a second controller of a second blood-donation system, the controller being configured, via the communication port, to receive status information of a blood-drawing session of the second blood-donation system, the controller located in or on a blood-donating chair;

initiating a first blood-drawing session at the first blood-donation system;

initiating a second blood-drawing session at the second blood-donation system, the second blood-drawing session being at least partially concurrent with the first blood-drawing session; and displaying status information of the first and second blood-drawing sessions at a display mounted on the blood-donating chair.

24. A blood-donation system comprising:

a blood-donating chair;

a plurality of mounting members on the blood-donating chair configured to mount and remount a plurality of donor-station devices; and a user interface mounted on the blood-donating chair, wherein the user interface sends commands to and/or receives data from at least several of the donor-station devices.

25. The blood-donation system according to claim 24, wherein the donor-station devices include at least one of:

a compressor cuff assembly;
a shaker assembly;
a tube clamp assembly;
a tube sealer assembly; or
a blood-bag identification scanner or reader.

26. The blood-donation system according to claim 24, wherein the blood-donating chair includes a power supply that supplies power to the several of the donor-station devices.

27. The blood-donation system according to claim 24, further including a controller affixed to or removable from the blood-donating chair, the controller having a communication port configured to operatively link with a second controller of a second blood-donation system, the controller configured to display status information from the second controller on the user interface.

* * * * *